US00PP32391P2

(12) United States Plant Patent
Leis et al.

(10) Patent No.: US PP32,391 P2
(45) Date of Patent: Oct. 27, 2020

(54) APPLE TREE NAMED 'CIVM49'

(50) Latin Name: ***Malus domestica* Borkh**
Varietal Denomination: CIVM49

(71) Applicant: C.I.V.—CONSORZIO ITALIANO VIVAISTI—SOCIETÀ CONSORTILE A R.L., Comacchio FE (IT)

(72) Inventors: Michelangelo Leis, Ferrara (IT); Alessio Martinelli, Ferrara (IT)

(73) Assignee: C.I.V.—CONSORZIO ITALIANO VIVAISTI—SOCIETA CONSORTILE A R.L., Comacchio (IT)

( * ) Notice: Subject to any disclaimer, the term of this patent is extended or adjusted under 35 U.S.C. 154(b) by 0 days.

(21) Appl. No.: 16/501,860

(22) Filed: Jun. 20, 2019

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875
See application file for complete search history.

(56) References Cited

PUBLICATIONS

Printout of application information from UPOV Pluto Database for corresponding CPVO application No. 2017/1992 filed Aug. 10, 2017, <http://www.upov.int/pluto/en/>, 1 page.

*Primary Examiner* — Kent L Bell
(74) *Attorney, Agent, or Firm* — Foley & Lardner LLP

(57) ABSTRACT

A new and distinct *Malus domestica* Borkh apple tree variety named 'CIVM49' is particularly characterized by resistance to scab. The tree has a very precocious bearing and medium vigor with high and constant productivity. The fruits are very attractive with uniform brilliant deep red color which covers the 80% of the surface. It has a very high eating quality, the flesh is crisp, juicy and tasty with high sweetness and medium-low acidity. Excellent storability and shelf life. Ripening time: 10/15 days after Gala.

4 Drawing Sheets

Figure 1:
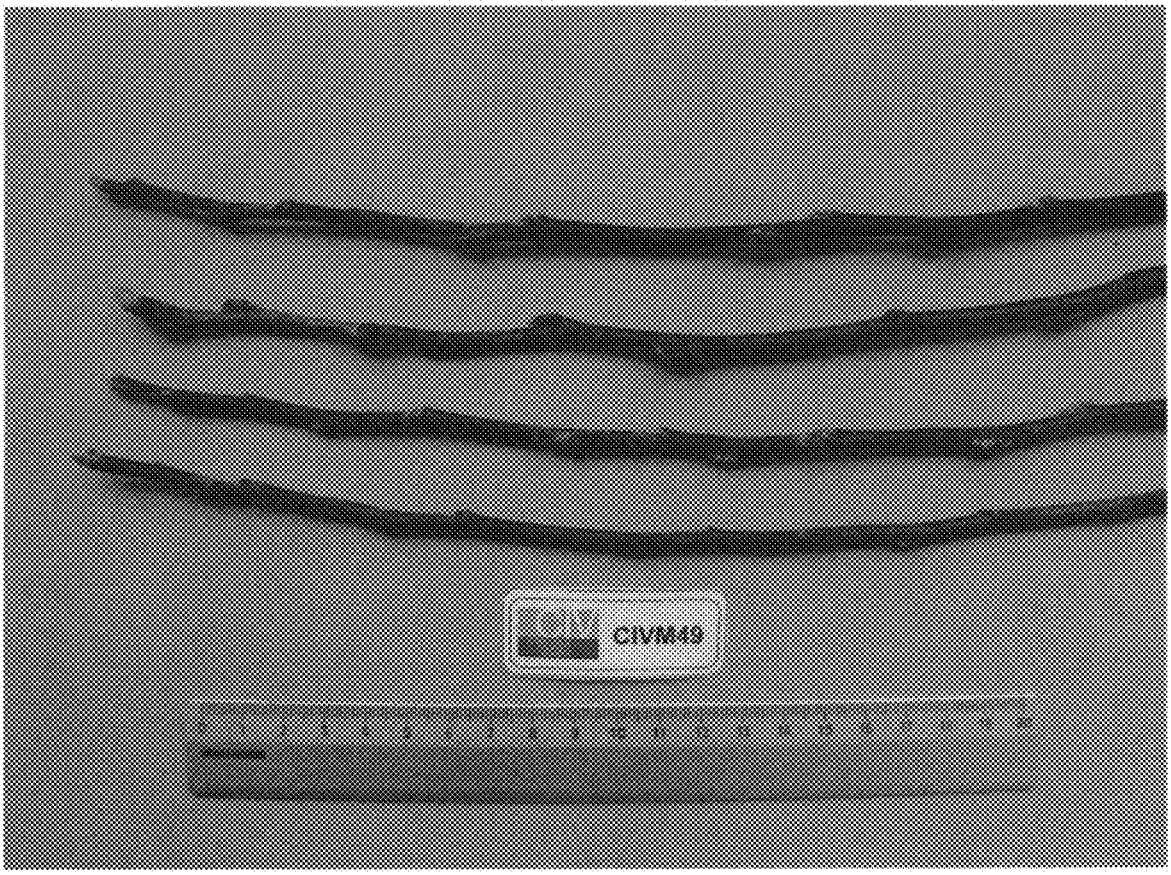

Latin name of the genus and species of the plant claimed: *Malus domestica* Borkh.

Variety denomination: 'CIVM49'.

BACKGROUND OF THE INVENTION

The present invention relates to a new and distinct variety of Apple tree, botanically known as *Malus domestica* Borkh of the Rosaceae family, and hereinafter referred to by the variety denomination 'CIVM49'.

The new *Malus* variety is a product of a planned breeding program conducted by the inventors, Michelangelo Leis and Alessio Martinelli, in San Giuseppe di Comacchio, Ferrara, Italy. The objective of the breeding program was to select and develop a new *Malus* variety with improved productions and sustainability by increasing the tree's natural resistance, very precocious bearing, high and constant productivity. The new varieties had to have very attractive fruits with uniform and deep red color which covers at least the 80% of the surface. The fruit had to have a crispy, juicy flesh with high sweetness and medium-low acidity with high firmness.

The new *Malus* variety, 'CIVM49' originated from a cross made by the inventors in 2000 in San Giuseppe di Comacchio (Ferrara), Italy. The female or seed parent is a patented variety denominated 'CO-OP39' (U.S. Plant Pat. No. 16,622). The male or pollen parent is an unpatented variety denominated 'MITCHGLA'. The new *Malus* variety 'CIVM49' was discovered and selected by the inventors within the progeny of the stated cross in a controlled environment in August 2006 in San Giuseppe di Comacchio (Ferrara), Italy.

Asexual reproduction of the new *Malus* variety 'CIVM49' by budding and grafting was first performed in September 2006 in San Giuseppe di Comacchio (Ferrara), Italy, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'CIVM49' which in combination distinguish this Apple tree as a new and distinct variety:

1. Resistant to scab;
2. Very precocious bearing;
3. Uniform and deep red color;
4. Very high eating quality with high level of sugar; and
5. Excellent storability and shelf life.

In comparison to the parents, 'CIVM49' differs primarily in the traits listed in Table 1.

TABLE 1

| Trait | New Variety 'CIVM49' | Female Parent 'CO-OP39' (U.S. Plant Pat. No. 16,622) | Male Parent 'MITCHGLA' (Unpatented variety) |
|---|---|---|---|
| Resistance to scab | Yes | Yes | Not |
| Fruit: hue of over color | Purple red | Red | Red |
| Fruit: pattern of over color | Solid flush with weakly defined stripes | Only solid flush | Only stripes |
| Time of eating maturity | Medium to late | Late | Medium |

Of the many commercial varieties known to the present inventors, the most similar in comparison to the new *Malus* variety named 'CIVM49' is the unpatented *Malus* variety 'MITCHGLA', in the following characteristics described in Table 2.

TABLE 2

| Characteristic | New Variety 'CIVM49' | Comparison Variety 'MITCHGLA' (Unpatented variety) |
|---|---|---|
| Time of eating maturity | Medium to late | Medium |
| Relative area of over color | Very large | Medium |
| Pattern of over color | Solid flush with weakly defined stripes | Only stripes |
| Resistance to scab | Yes | Not |

BRIEF DESCRIPTION OF THE PHOTOGRAPHS

The accompanying photographs illustrate the overall appearance of the new *Malus* variety 'CIVM49' showing the colors as true as is reasonably possible with colored reproductions of this type. Colors in the photographs may differ slightly from the color values cited in the detailed botanical description, which accurately describe the color of a 7-year-old tree of 'CIVM49'.

Figure 2:
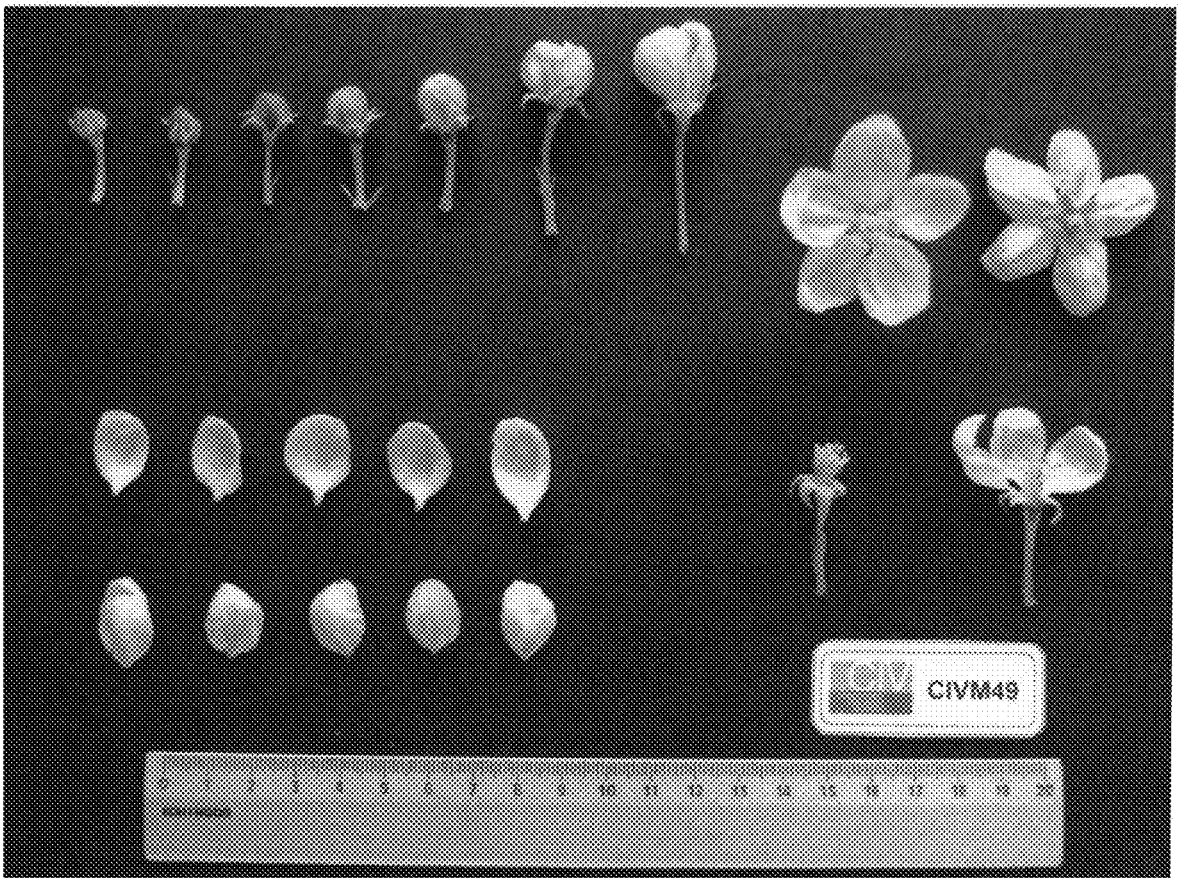
Figure 3:
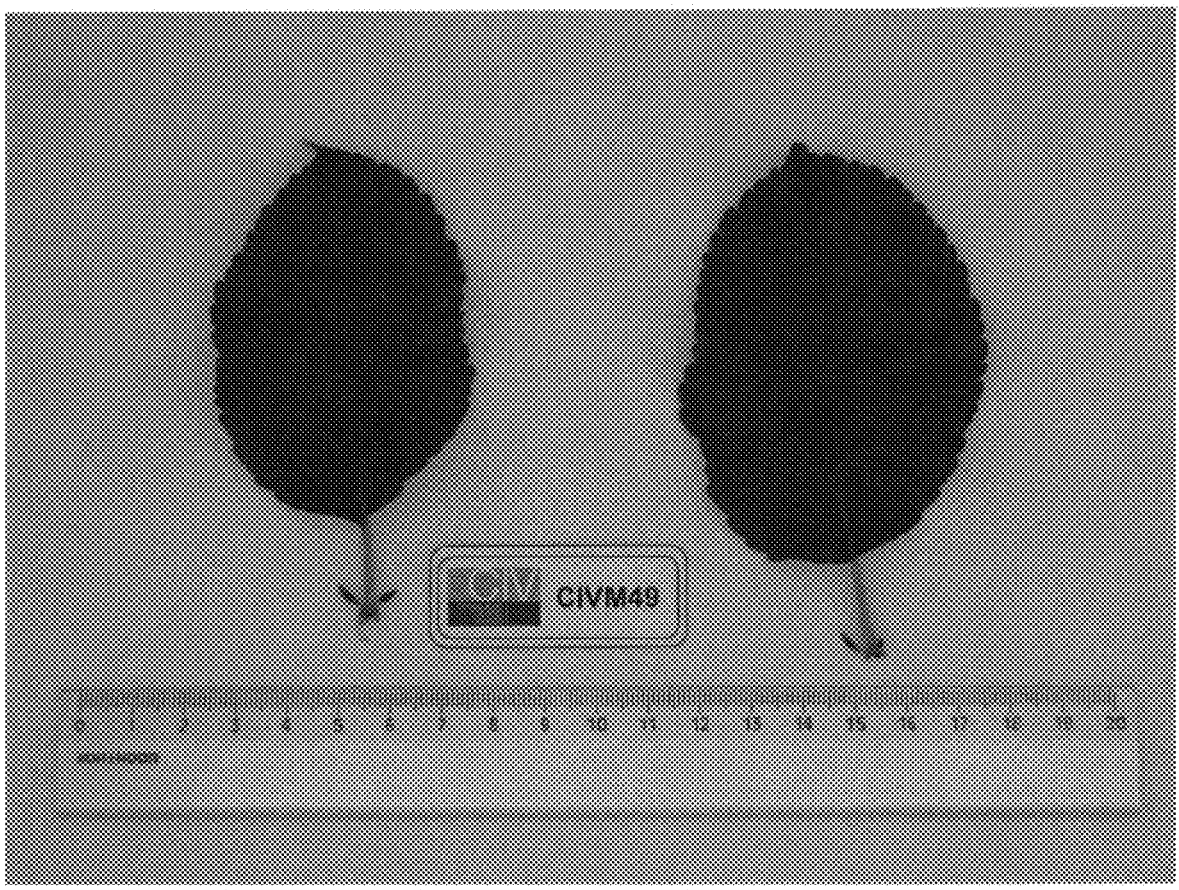
Figure 4:
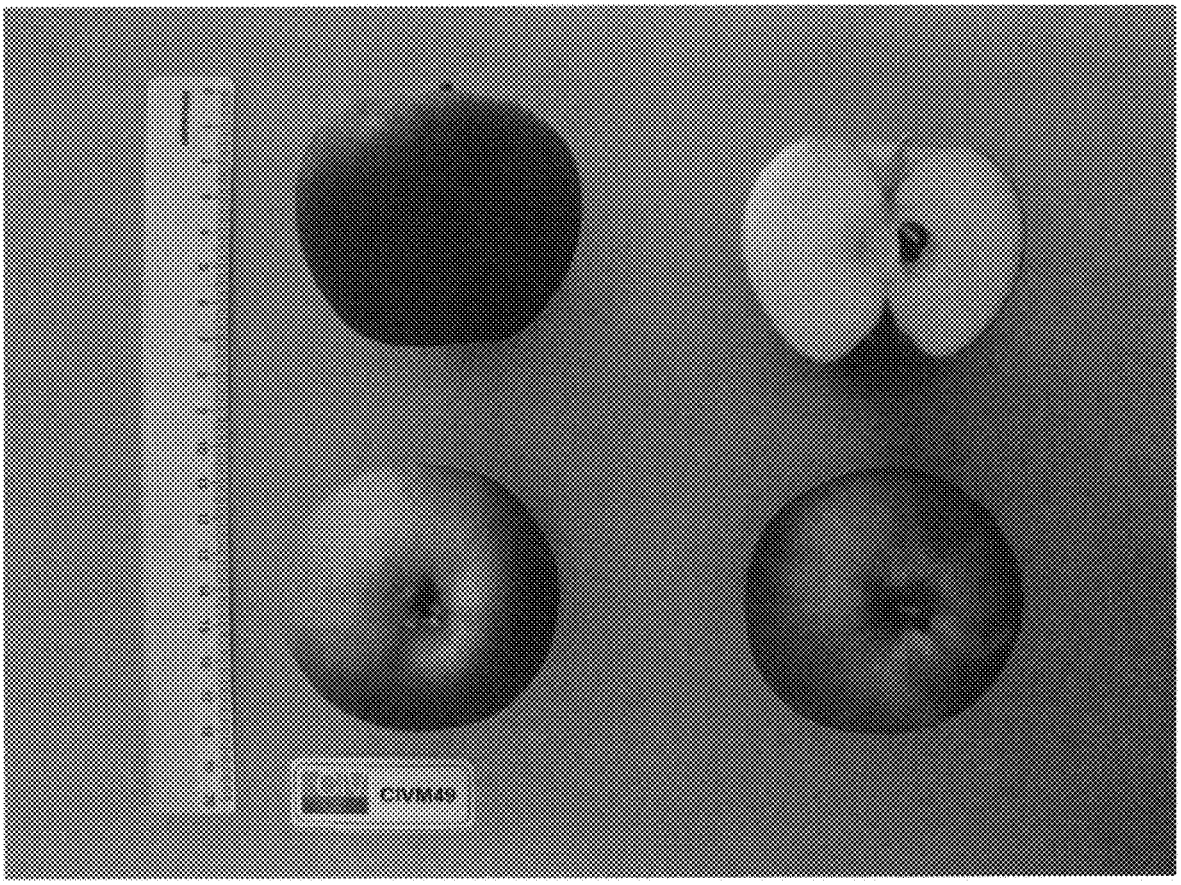

FIG. 1—Illustrates typical dormant wood of 'CIVM49';
FIG. 2—Illustrates typical flowers of 'CIVM49';
FIG. 3—Illustrates typical leaves of 'CIVM49';
FIG. 4—Illustrates typical fruits of 'CIVM49'.

DETAILED BOTANICAL DESCRIPTION

The new *Malus* variety 'CIVM49' has not been observed under all possible environmental conditions. The phenotype of the new variety may vary with variations in environment such as temperature, light intensity, and day length without any change in the genotype of the Apple tree.

The aforementioned photographs, together with the following observations, measurements and values describe trees of 'CIVM49' as grown in the Apple farm in San Giuseppe di Comacchio (Ferrara), Italy, under conditions which closely approximate those generally used in commercial practice. The apple farm where 'CIVM49' grows, is situated near the Adriatic Sea (44° 45' North, 12° 11' East) and is zero (0) meters above sea level. The soil of the apple farm where 'CIVM49' is grown is sandy, and the soil is treated with manure every year and irrigated with drip irrigation system. The climate is temperate continental with high summer temperatures and low winter temperature.

Unless otherwise stated, the detailed botanical description includes observations, measurements and values based on seven (7) year old 'CIVM49' trees grown in the Apple farm in San Giuseppe di Comacchio (Ferrara), Italy from 2012. Quantified measurements are expressed as an average of measurements taken from a number of ten (10) trees of 'CIVM49'. Color references are made to The Royal Horticultural Society Color Chart (R.H.S.), 2001 edition, except where general colors of ordinary significance are used. Color values were taken under daylight conditions at approximately at 10:00 A.M. in San Giuseppe di Comacchio (Ferrara), Italy.

All of the trees of 'CIVM49', insofar as they have been observed, have been identical in all the characteristics described below.

Classification:

*Botanical.*—*Malus domestica* Borkh.

Parentage:

*Female or seed parent.*—*Malus* patented variety denominated 'CO-OP39' (U.S. Plant Pat. No. 16,622).

*Male or pollen parent.*—*Malus* unpatented variety denominated 'MITCHGLA'.

Propagation: Budding and grafting.

Growing conditions:

*Light intensities.*—Full sunlight.

*Temperature.*—The variety 'CIVM49' was tested in S. Giuseppe di Comacchio (Ferrara), Italy where the temperature range is from −6° C. to 38° C.

*Fertilization.*—The soil is sandy, treated with manure every year. With fertigation we make macroelements (N 100 u/ha; P 100 u/ha; 200 K u/ha) and microelements.

*Growth regulators.*—No.

*Pruning or trimming requirements.*—Yes.

Tree:

*Age.*—Observed trees were 7 years old.

*Vigor.*—Medium vigor.

*Form.*—Ramified.

*Habit.*—Spreading tree with one trunk and one leader.

*Branching habit.*—Main branches angle is about 80° to 85° with respect to trunk if allowed to grow naturally.

*Density.*—High density.

*Cropping behavior.*—Very early beginning production, high productivity and abundant flowering. Not biennial bearing.

*Type of bearing.*—Long shoots and spurs.

*Production.*—Seven (7) year old trees, 11 Kg/tree (The distance of planting is 3.3 m×0.80 m about 3.800 plant/Ha).

*Size at maturity.*—Height: Average 3.2 m. Spread: Average 1.1 m.

*Trunk.*—Diameter: 50 mm, measured at 20 cm above point of grafting. Texture: Smooth. Bark color: Primarily RHS 197 B greyed-green group. Trunk Lenticels: Length: About 4.0 mm. Width: About 1.0 mm. Color: RHS 164 A greyed-orange group. Density: About 1.4 per $cm^2$.

*Branches.*—Number per tree: About 14. Length: Varies due to pyramidal shape of tree. Maximum of 77 cm to minimum of 25 cm. Diameter (at 3 years): About 12 to 16 mm. Surface texture: Smooth. Color:

Mature (three (3) year old): RHS 197 B greyed-green group. New Growth: RHS 166 A greyed-orange group. Internode length: 30 to 40 mm. Internode diameter: 10 to 12 mm. Branch lenticels: Length: About 1.1 mm. Width: About 0.3 mm. Color: RHS 167 D greyed-orange group. Density: About seven (7) per $cm^2$.

*Spur*.—Present: Yes. Distance between each spur: On two/three year old branches, the distance is 25 mm to 35 mm. Diameter of each spur: About 5.3 mm. Number of fruits per spur: 4 to 5 without thinning.

*Buds*.—Terminal Buds: Number per spur: typically, one per spur. Shape: Pointed. Length: About 9 mm. Width: About 4 mm. Texture: Hairy. Color: RHS 177 B greyed-orange group.

*Lateral buds*.—Number per spur: 3/4. Shape: pointed. Length: About 3.9 mm. Width: About 2.6 mm. Texture: smooth. Color: RHS 187 A greyed-purple group.

Foliage:

*Arrangement*.—Alternate, simple, petiolate.

*Lamina*.—Size: Length: Average 84 mm (from $3^{rd}$ to $5^{th}$ fully expanded leaf). Width: Average 55 mm (from $3^{rd}$ to $5^{th}$ fully expanded leaf). Length/width ratio: 1.5.

*Overall shape*.—Elliptic to rounded. Base shape: Broad. Apex shape: Broad with acuminated tip. Margin: Crenate. Texture: Upper surface: Smooth. Under surface: Hairy. Attitude in relation to shoot: Outwards. Color (mature leaves): Upper surface: RHS 137 A green group. Under surface: RHS 137 D green group. Color (immature leaves): Upper surface: RHS 144 A yellow-green group. Under surface: RHS 146 B yellow-green group.

*Venation*.—Type: prominent pinnate venation from a midrib to the edge. Color: yellow-green (RHS 144 D).

*Petiole*.—Length: Average 17 mm. Diameter: Average 1.6 mm. Texture: Smooth. Color: yellow-green (RHS 144 C).

*Stipule*.—Arrangement: Adnate, grown together. Length: About 4.6 mm. Width: About 0.9 mm. Color: Upper surface: RHS 138 A green group. Under surface: RHS 138 B green group.

Flower:

*Blooming time*.—Full bloom on April $5^{th}$ in San Giuseppe di Comacchio (Ferrara), Italy in year 2018.

*Blooming period*.—About 8 to 10 days.

*Fragrance*.—Slight.

*Type*.—Corymb inflorescence.

*Number of flowers per inflorescence*.—5 to 6.

*Flower size*.—Medium, about 40 mm.

*Flower depth* (*height of the corolla*).—About 20 mm.

*Petals*.—Arrangement: Free to intermediate. Number per flower: Five. Size: Length: About 21 mm. Width: About 14 mm. Length/width ratio: 1.5. Overall shape: Elliptic to ovate. Apex shape: Rounded. Base shape: Broad. Texture (upper surface): Smooth. Texture (lower surface): Smooth. Margin: Entire. Color (upper surface): White (RHS 155D white group). Color (lower surface): White (RHS 155D white group), with red purple shades (70B red-purple group).

*Sepals*.—Number per flower: Five (5). Size: Length: Average 9 mm. Width: Average 3 mm. Length/width ratio: 3. Overall shape: Lanceolate. Apex shape: Acute. Base shape: Broad. Texture (upper surface): Hairy. Texture (lower surface): Hairy. Margin: Entire. Color (upper surface): Green (RHS 144 C yellow-green group). Color (lower surface): Green (RHS 144 A yellow-green group).

*Pedicel*.—Length: 26 to 45 mm. Diameter: about 1.0 mm. Texture: Hairy. Color: Green (RHS 144 A yellow-green group).

Fruit:

*Keeping quality*.—The fruit keeps very well on the tree. It can be stored in cold temperature conditions without losing firmness and juiciness. It has a good shelf life, up to two weeks.

*Maturity when described*.—Ripe for eating.

*Maturity period after full bloom*.—About 142 days in San Giuseppe di Comacchio, Ferrara, Italy.

*Date of first and last picking* (*harvest*).—August $26^{th}$ to September $14^{th}$ in S. Giuseppe di Comacchio (Ferrara) Italy in year 2018.

*Type*.—Pome.

*General shape*.—Conic.

*Average weight*.—Average 146 g.

*Fruit size*.—Average height: 60 mm. Average diameter (at widest point): 70 mm. Position of maximum diameter: ¾ of height near stem. Height/thickness ratio: 0.86.

*Stem*.—Length: Average 18.0 mm. Diameter: Average 2.0 mm. Color: RHS 151 A yellow-green group.

*Stalk cavity*.—Depth: Average 13.0 mm. Width: Average 31.6 mm.

*Eye basin*.—Depth: Average 11.0 mm. Width: About 28.0 mm. Crowning at calyx end: Weak. Position of sepals: Open. Calyx tube: Funnel form.

*Skin*.—Thickness: Medium. Texture: Smooth. Bloom: Absent. Greasiness: Absent. Firmness (at picking time): About 9.0 kg/$cm^2$. Overcolor Color: Purple red (RHS 53 A red group). Percentage of skin surface with overcolor color: About 80%. Pattern of overcolor: Solid flush with weakly defined stripes. Intensity of overcolor: Medium to dark. Ground color: Yellow (RHS 21A orange group). Skin Lenticels: Length: About 0.6 mm. Width: About 0.6 mm. Color: RHS 17A yellow-orange group. Density: About 5 per $cm^2$ measured in the central area of the surface of fruit.

*Flesh*.—Color: Cream (RHS 8 D yellow group). Texture: Fine. Aroma: Aromatic. Eating quality: Good flavor with high level of sugar. Sugar content (at picking time): Average 14.5° to 15° Brix. Acidity/Starch (at picking time) Average 4.9 g/lt Acid Malic. Core: Symmetry of core: Symmetric. Distinctness of core lines: Weak. Locules: Number (per fruit): 5. Length: Average 8.9 mm. Width: Average 8.7 mm. Form: Closed or moderately open.

Seeds:

*Number per fruit*.—8 to 10.

*Number per locule*.—2.

*Shape*.—Elliptic, elongated and pointed.

*Length*.—Average 7.1 mm.

*Width*.—Average 4.9 mm.

*Texture*.—Smooth.

*Color*.—RHS 166A greyed-orange group.

Reproductive organs:

*Androecium*.—Pistil: Number per flower: 5. Length: Average 3.92 mm. Width: Average 0.33 mm. Color: RHS 149 B yellow group. Stamen: Number per flower: About 19. Length: Average 6.9 mm. Color: RHS 155D white group. Anther: Shape: Ovoid. Length: Average 2.5 mm. Color: Yellow (RHS 11B yellow group). Filaments: Length: Average 19 mm. Color: RHS 155D white group. Pollen: Amount: Medium. Color: RHS 11 B yellow group. Pollination Requirements: the crab apple variety 'Golden Gem' is a good pollinator.

*Gynoecium*.—Stigmas: Shape: Funnel shape with receptive surface on top. Length: Average 1.4 mm. Width Average 0.6 mm. Color: RHS 149 B yellow-green group. Ovary: Length: Average 5.3 mm. Width: Average 3.5 mm. Color: RHS 184 B greyed-purple group.

Use: Fresh market.

Disease/pest resistance: Scab resistant. DNA analysis shows the presence of WINTER HARDINESS: Tolerant to temperatures of −7° C. without observed damage to wood and buds of dormant trees; but open flowers and young fruitlets are killed by exposure to −3° C., depending on the length of exposure.

Drought/heat tolerance: Tolerant to temperatures of 38° C., growth is limited by drought periods without irrigation.

Storage characteristics: Good storability in controlled atmosphere (1.2-1.3° C., 1.2% $0_2$, 0.4% $CO_2$) for six (6) months.

We claim:

1. A new and distinct variety of *Malus domestica* Borkh apple tree named 'CIVM49', as illustrated and described herein.

* * * * *